Figure 1:
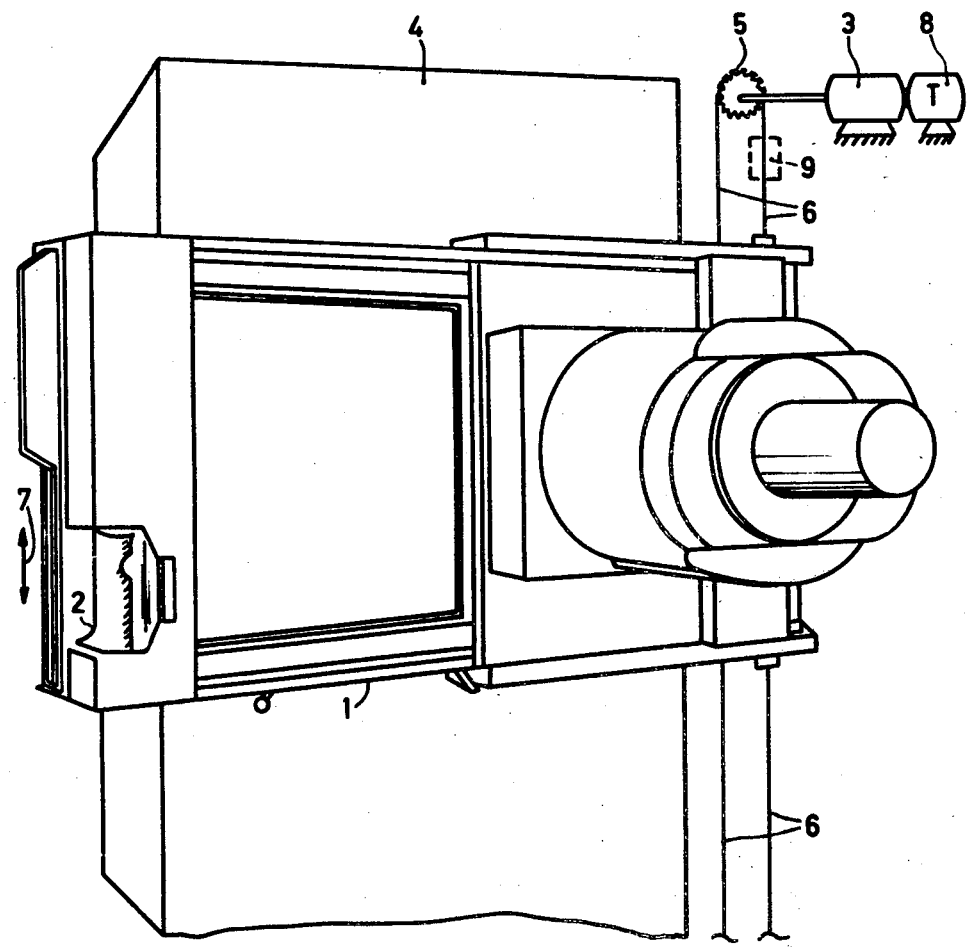

United States Patent

Von Hacht et al.

[11] 4,021,715
[45] May 3, 1977

[54] MOTOR DRIVE FOR THE DISPLACEMENT OF A SECTION OF AN X-RAY EXAMINATION APPARATUS

[75] Inventors: Reinhard Von Hacht, Halstenbek; Klaus Rennicke, Rellingen; Walter Schmedemann, Hamburg, all of Germany

[73] Assignee: U.S. Philips Corporation, New York, N.Y.

[22] Filed: Jan. 9, 1975

[21] Appl. No.: 539,699

[30] Foreign Application Priority Data
Jan. 16, 1974  Germany .......................... 2401853

[52] U.S. Cl. ............................. 318/628; 318/327; 250/449; 250/525
[51] Int. Cl.$^2$ ...................................... G01N 21/34
[58] Field of Search ........... 250/449, 525; 318/327, 318/431, 488, 628

[56] References Cited
UNITED STATES PATENTS

| | | | |
|---|---|---|---|
| 3,013,155 | 12/1961 | Schiring | 250/499 |
| 3,215,835 | 11/1965 | Mueller | 250/499 |
| 3,245,285 | 4/1966 | Kieboom | 318/488 UX |
| 3,458,791 | 7/1969 | Boice | 318/327 |
| 3,866,048 | 2/1975 | Gieschen et al. | 318/628 X |

*Primary Examiner*—B. Dobeck
*Attorney, Agent, or Firm*—Frank R. Trifari

[57] ABSTRACT

A motor drive for an X-ray examination apparatus, in particular for the displacement of an auxiliary apparatus (imaging section). The motor has coupled thereto a tachometer, the output signal of which is differentiated and fed back to the motor control system such that a positive loop gain < 1 arises. The drive system delivers a torque which is proportional to the force delivered by the operator when a linear relationship exists between the control quantity of the motor and the torque thereof. In the case of a collision with the patient, the force exerted by the imaging section on the patient substantially does not exceed the manual force exerted by the operator, not even if the motor force amounts to a multiple of the force delivered by the operator.

7 Claims, 3 Drawing Figures

MOTOR DRIVE FOR THE DISPLACEMENT OF A SECTION OF AN X-RAY EXAMINATION APPARATUS

The invention relates to a motor drive to be used in an X-ray examination apparatus for the displacement of a section of the apparatus, notably an imaging section, the speed and the direction of rotation of the motor being controllable in dependence of the value and the direction of a manual force acting on the section, a tachometer forming a signal proportional to the speed, the said signal also serving for the control of the motor, a further control signal being applied to the motor circuit in order to compensate for the weight of the section.

The introduction of the image intensification technique, of automatic exposure devices, etc., for diagnostic X-ray examinations has resulted in an increased weight of the imaging section because of the addition of new apparatus. Even though the weight forces to be overcome can be compensated for by counterweights, the person performing the examination must accelerate or decelerate also this mass when the imaging section is moved, which implies that a substantial amount of physical labor is required from him in the course of a working day. Therefore, various motor drives have already been developed to take over the work of the operator in this respect.

For example, motor drives are known in which the speed of the motor and hence also the speed of displacement of the imaging section or the force exerted by the motor on the imaging section are dependent on the force exerted by the operator on a grip of the imaging section. The grip is then coupled to a transducer which supplies a signal to control the speed or the force delivered by the motor.

This motor drives substantially assist the operator, but the motor drives do not react when the imaging section collides with an obstacle, for example, a patient. The patient is then liable to incur substantial injury if no special, expensive safety measures are taken.

Also known is a motor drive for an X-ray examination apparatus which does not have the latter drawback and in which the drive energy for the drive motor can still be controlled by way of the force exerted on the section to be displaced (an imaging section).

However, this known drive has the drawback that the energy generated in dependence of the force acting on the imaging section is independent of whether the force is active in the direction of gravity or in the opposite direction. Consequently, the movement behavior of the imaging section differs in these two directions and is substantially dependent of the weight of the imaging section and the components each time connected thereto. In the known device the imaging section to be displaced is connected to a counterweight by way of a beam of balance, with the result that the beam of balance, movable against the action of a spring, is compensated. When a force is exerted on the imaging section, the beam of balance leaves its rest position, the motor power then being changed in dependence of the deviation of the beam of balance from its rest position. Because of the springs required for determining the value of the force exerted on the imaging section, however, the motor drive is liable to oscillate.

A further motor drive for putting a section of an X-ray examination apparatus into motion is known, in which a transducer, for example, a strain gauge or a quartz crystal, is arranged such that it produces a signal which is dependent of the force exerted on the section and of the weight thereof. The transducer signal is reduced by a signal which corresponds to the weight and which serves as a target value for the speed control of the motor. Speed control is effected by means of a tachometer which supplies a signal which is dependant of the speed and of the direction of rotation of the motor and which is fed back to the input as a control signal (German Auslegeschrift No. 2,104,509). The speed of the motor, and hence the speed at which the motor displaces the imaging section, is then determined by the manual force. In this apparatus part of the motor torque is utilized to compensate for the weight of the imaging section. The remainder of the motor torque serves, together with the manual force, for the acceleration of the imaging section, however, is smaller than the manual force of the operator alone. Therefore, the operator does not receive any real assistance from the servomotor drive; on the contrary, when displacing the imaging section, having a weight of up to 200 to 300 kg in contemporary X-ray examination apparatus, the operator himself must deliver the force for the acceleration and for overcoming the friction.

The invention has for its object to provide a motor drive for the displacement of a section of an X-ray examination apparatus such that the contribution made by the motor in overcoming the acceleration and friction forces can be larger than the power delivered by the operator, that the motor drive reacts, however, should the section collide with an obstacle, that no vibrations occur when the motor drive is switched on, and that the section is movable in each direction in the same manner in dependence of the manual force.

The motor drive according to the invention is characterized in that the output signal of the tachometer is applied to the motor drive via a differentiating member, the loop gain in the loop formed by the tachometer, the differentiating member and the motor drive being positive and smaller than 1.

When the operator displaces the section of an X-ray examination apparatus by means of the motor drive according to the invention, a tachometer signal is produced which is differentiated by the differentiating member and applied to the motor drive. The motor drive thus receives a control signal which is proportional to the differential quotient of the speed with respect to the time and which changes the torque of the motor for the given polarity of the loop gain such that the movement of the section initiated by manual force is assisted.

In the simplest case the signal for controlling the motor is thus composed of the input signal of the differentiating member and a direct current portion which is proportioned in known manner (Swiss patent specification No. 2,252,448, FIG. 6) such that in the rest state, i.e., when no further forces (except for the force of gravity) act on the section, the torque of the motor is exactly adequate to keep the section balanced so that no separate counterweights are required. (If counterweights are used, the direct current control signal can obviously be dispensed with). The special advantage of this simple embodiment is that no separate transducers are required, which is in contrast with all other described motor drives, so that any cut-outs of the motor due to a fault in the transducer are precluded. In any case, the torque delivered by the motor for the acceleration of the section is substantially dependent on the characteristic of the motor, i.e, of the ratio between torque and control quantity. A constant ratio between the torque especially delivered by the motor for the acceleration of the section and the manual force delivered by the operator can be achieved only —and it is only in the case of a constant ratio between the motor force and the force delivered by the operator that the operator will not notice the motor drive, which is particularly desirable — if there is a linear relationship between the control quantity and the motor torque. Further preferred embodiments according to the invention in which a linear relationship is formed between the control quantity of the motor and the torque thereof are described in the claims.

A further preferred embodiment according to the invention requires a transducer, but this embodiment offers the advantage that — if the transducer is connected in known manner (German Auslegeschrift No. 2,104,509) to the wire transferring the motor force to the section — the operator need not overcome the total friction force when the section is put into motion from standstill, but only a fraction thereof in accordance with the assistance given by the motor. Moreover, the loop incorporating the transducer operates in the sense of a feedback, so that non-linearity between control quantity and motor torque is at least partly compensated for, with the result that, unlike in the embodiments without transducer, it is not so important to have a motor drive involving a linear relationship between control quantity and torque.

The invention will be described in detail hereafter will reference to some embodiments which are diagrammatically shown in the drawing.

Figure 2:
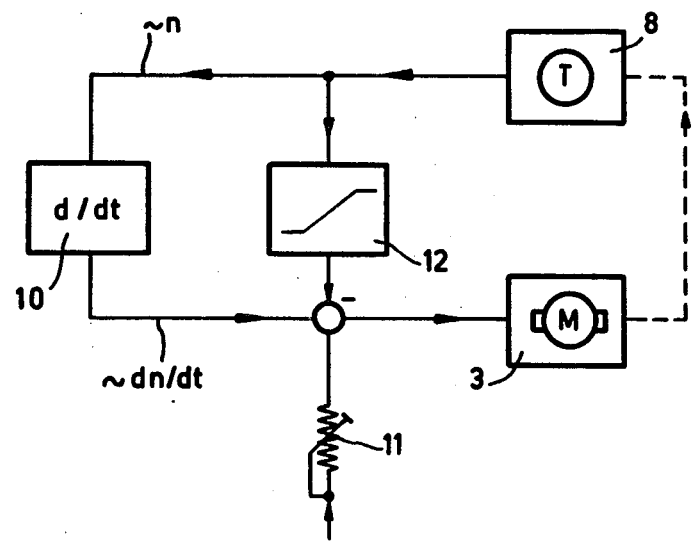
Figure 3:
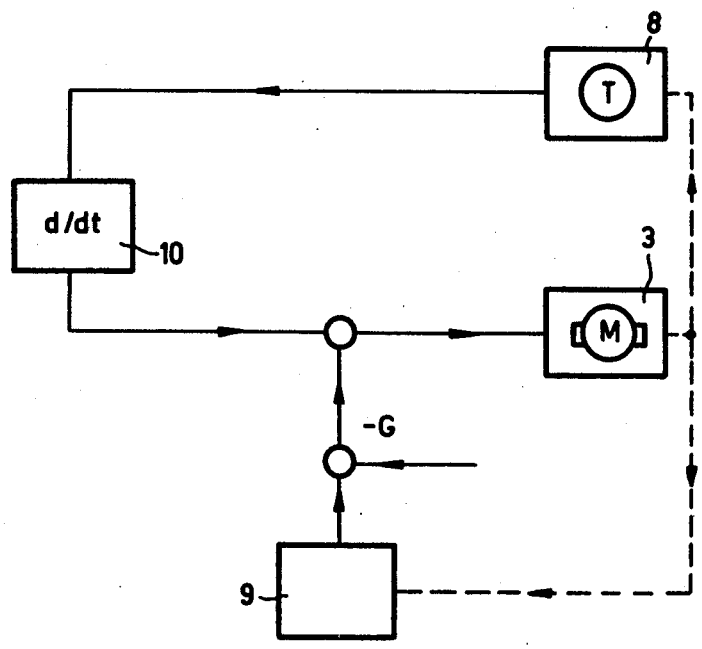

FIG. 1 shows an X-ray examination apparatus, comprising a motor drive for the displacement of the X-ray imaging section in the longitudinal direction, FIG. 2 shows a block diagram of an embodiment according to the invention without transducer, and FIG. 3 shows a block diagram of an embodiment including a transducer.

FIG. 1 shows an X-ray imaging section 1 which is movable in the direction of the arrow 7 by way of a grip 2. The imaging section 1 is connected to a wire or chain 6 which is guided over pinion 5 at the top of the examination apparatus 4 (diagrammatically shown only in part in this figure) and over a second pinion which is not shown and which is provided underneath the examination apparatus. Provided as an aid for the operator is a motor 3 which drives the pinion 5 and also a tachometer 8. In the embodiment including a transducer, in the portion of the chain situated between the pinion 5 and the imaging section 1 there is included a transducer 9 (denoted by a broken line) in the form of a strain gauge, an inductive transducer or a quartz crystal.

According to FIG. 2, the tachometer 8 applies a voltage proportional to the speed $n$ to the input of a differentiating member 10, the output signal of which is proportional to the differential quotient of the speed with respect to the time ($dn/dt$) and serves as a control quantity for the motor 3. Because the shaft of the motor 3 is mechanically coupled to the tachometer shaft, the tachometer output signal is also influenced thereby, as indicated by the arrow (broken line) between the motor 3 and the tachometer.

The tachometer 8, differentiating member 10 and the motor 3 thus form a closed loop, the loop gain of which is positive according to the invention. When the imaging section is moved by the operator, the tachometer 8 supplies an output signal, the differential quotient of which influences the motor 3 which then delivers an (additional) torque such that the movement indicated by the operator is assisted by the motor. This assistance is greater as the loop gain is higher. Should the imaging section collide with an obstacle, for example, the chin of the patient, the movement of the imaging section is decelerated thereby. As a result, the output signal of the tachometer decreases and the output signal of the differentiating member changes its sign, with the result that the motor decelerates the movement of the imaging section, it being possible for the deceleration force to exceed the force exerted on the imaging section by the obstacle, depending on the loop gain in the loop 3, 8, 10.

If the loop gain is smaller than 1, the system is stable. The fluctuations in the parameters of the elements incorporated in the loop (in the case of a direct current motor, for example, the fluctuation in the starting current, depending on the field resistance and hence on the temperature), however, necessitates observing a safety margin as regards this critical value of the loop gain. Changes in the mass of the section, for example as caused by the mounting of an additional apparatus on the imaging section, also influence the stability. If these changes of the mass are substantial, they must be taken into account. They can be determined by way of a measurement, and can influence the loop gain by way of adaptive control. To this end, an amplifier having an adjustable gain factor can be included in the loop consisting of the elements 3, 8 and 10. The gain thereof can possibly also be adjusted by hand for adaptation each time to the given mass of the imaging section.

The ratio between the torque delivered by the motor for the acceleration of the imaging section and the force delivered by the operator is substantially dependent of the relationship between the control quantity on the input of the motor 3 and the torque delivered by the motor. If a linear relationship exists between the control quantity on the input of the motor and the torque thereof, the ratio between the force delivered by the operator and the motor torque for the acceleration of the imaging section is constant. Such a constant ratio should be pursued because then the operator will not at all feel assisted by a motor and because then the mass to be accelerated by the operator apparently becomes smaller. Like in apparatus without motor assistance, the operator then has the feeling that the movement of the imaging section depends only on the force he exerts on the imaging section. However, his work is actually facilitated in that a substantial part of the force required for the acceleration of the section is delivered by the motor.

In order to obtain a linear relationship between the control quantity and the motor torque, it is advantageous to use a direct current shunt motor, because the torque thereof has a linear relationship with the armature current. Therefore, when the output signal of the differentiating member is applied to the direct current shunt motor as armature current, the desired linear behavior, and hence a constant ratio between the force delivered by the operator and the assistance received from the motor force (in the case of constant power supply and constant voltage on the terminals), is very closely approximated already. However, the armature current is then influenced by the speed-dependent armature voltage. This influence can be eliminated by armature current control. The output signal of the differentiating member 10 then serves as a target value for the armature current control. The effect of the armature feedback on the linearity can be suppressed by using a motor incorporating a compensation winding or by torque control, the torque being taken directly from the motor shaft and being compared with the target value (the output signal of the differentiating member), possible deviations then being eliminated by control.

In the absence of a counterweight, the motor must deliver the torque which is necessary to keep the imaging section in its relevant position when it is in standstill, i.e. when the operator does not exert a force on the imaging section. To this end, the output signal of the differentiating member has superimposed thereon a direct voltage or direct current signal which is porportioned such that during standstill the motor keeps the imaging section in the position occupied at that instant. By means of a variable resistor 11, this static control quantity can be adapted to changes in the weight of the imaging section which are caused, for example, by the addition of an extra apparatus to the imaging section.

It may be desirable to adjust the maximum speed at which the image section can be moved in order to limit the forces which can occur upon collision with an obstacle. To this end, the output of the tachometer is connected to a threshold circuit 12, the output signal of which is also superimposed on the output signal of the differentiating member 10. The threshold circuit supplies an output signal having a polarity which is chosen such that the output signal of the differentiating member is decreased, but only if the output voltage of the tachometer 8 exceeds a given value.

Because the motor drive shown in FIG. 2 becomes effective only if a signal appears on the output of the tachometer, i.e., when the imaging section has already started to move, the operator must first overcome the frictional forces (static friction) in order to put the imaging section into motion. In the case of imaging sections having an unfavorable construction, these friction forces may be comparatively high. In order to prevent the operator from having to overcome the full friction forces, a voltage having a suitable value and a polarity which is dependent of the direction of displacement can be briefly superimposed on the output signal at the beginning of the apparatus movement. For this purpose the grip 2 of FIG. 1, normally constructed as a brake grip, could have switches coupled thereto which react to a pressure from the grip in the upward or downward direction and which switch over the polarity of the signal to be briefly superimposed accordingly.

FIG. 3 shows an embodiment having a separate transducer. The components which have the same function as in the block diagram of FIG. 2 are denoted by the same references. The signal paths which serve for limiting the maximum speed and for the static compensation of the weight of the imaging section and which are routed via the blocks 12 and 11 have been omitted for the sake of simplicity. However, they can obviously also be used in the circuit arrangement shown in FIG. 3. A transducer 9, inserted in the portion of the wire 6 between the pinion 5 and the imaging section 1 (see FIG. 1), supplies a signal which is proportional to the force in the wire or chain. In the rest position the weight G of the imaging section acts on the transducer 9 which thus supplies a signal corresponding to the weight G of the imaging section. This static component of the signal supplies by the transducer 9 can be compensated for by a direct voltage which corresponds to the weight G of the apparatus and which can be adapted in known manner to a variation of the forces acting on the transducer in the rest state, such a variation occurs, for example, when an extra apparatus is added to the imaging section. When the imaging section is moved, the transducer is not only influenced by the apparatus weight but also by the manual force and the forces delivered by the motor for accelerating the imaging section and for overcoming the friction of the imaging section. The output signal of the transducer 9 is, therefore, also dependent of the torque of the motor, and because this output signal is superimposed on the output signal of the differentiating member 10 and hence influences this torque, a second closed loop is formed which comprises the motor 3 and the transducer 9 (denoted by the broken-line arrow between the motor 3 and the transducer 9). The loop gain, which may be adjustable by means of an amplifier having an adjustable gain (not shown), must be negative in this loop, so that in contrast with the first loop, having a positive loop gain and hence positive feedback, a negative feedback arises which operates in the sense of a control system. As a result, the relationship between the control quantity on the input of the motor 3 and the torque delivered thereby can be linearized. It is a further advantage that the transducer already supplies a signal before the imaging section starts to move. The static friction is thus overcome with the assistance of the motor.

What is claimed is:
1. A motor drive to be used in an X-ray examination apparatus for the displacement of a section of the apparatus, notably an imaging section, the speed and the direction of rotation of the motor being controllable in dependence of the value and the direction of a manual force acting on the section, a tachometer forming a signal proportional to the speed, the said signal also serving for the control of the motor, a further control signal being applied to the motor circuit in order to compensate for the weight of the section, characterized in that the output signal of the tachometer is applied to the motor drive via a differentiating member, the loop gain in the loop formed by the tachometer, the differentiating member and the motor drive being positive and smaller than 1.

2. A motor drive as claimed in claim 1, characterized in that the drive motor delivers a torque which is proportional to the control signal.

3. A motor drive as claimed in claim 2, characterized in that it comprises a direct current shunt motor, the armature current of which comprises a component which corresponds to the output signal of the differentiating member.

4. A motor drive as claimed in claim 3, chracterized in that an armature control system is provided for which the output signal of the differentiating member serves as a target value.

5. A motor drive as claimed in claim 2, characterized in that it comprises a torque control system for which, the target value is formed by the output signal of the differentiating member.

6. A motor drive as claimed in claim 1, characterized in that there is provided a transducer which supplies a signal which is dependent of the forces exerted on the section, the said signal being superimposed on the output signal of the differentiating member, the loop gain in the loop comprising the transducer and the motor being negative.

7. A motor drive as claimed in claim 1, characterized in that there is provided a threshold circuit which is controlled by the tachometer signal and which superimposes a signal on the output signal of the differentiating member when the tachometer output signal exceeds a predetermined amplitude, the said superimposed signal having a reducing effect on the output signal of the differentiating member.

* * * * *

UNITED STATES PATENT AND TRADEMARK OFFICE
CERTIFICATE OF CORRECTION

PATENT NO. : 4,021,715
DATED : May 3, 1977
INVENTOR(S) : REINHARD VON HACHT ET AL

It is certified that error appears in the above-identified patent and that said Letters Patent are hereby corrected as shown below:

Column 2, line 20, "section, however" should be --section. The total force for the acceleration of the imaging section, however--

Column 6, line 4, "supplies" should be --supplied--
line 8, "such" should be --. Such--

Signed and Sealed this second Day of August 1977

[SEAL]

Attest:

RUTH C. MASON
*Attesting Officer*

C. MARSHALL DANN
*Commissioner of Patents and Trademarks*